United States Patent [19]
Kato et al.

[11] Patent Number: 5,932,259
[45] Date of Patent: Aug. 3, 1999

[54] BONE REINFORCING AGENT AND FOODS AND DRINKS PRODUCT CONTAINING THE SAME

[76] Inventors: Ken Kato; Hiroaki Matsuyama, both of 11-3, Arajuku-cho 5-chome, Kawagoe; Yukihiro Takada, 62-22, Kozutsumi, Kawagoe; Toshiaki Uchida, 11-3, Arajuku-cho 5-chome, Kawagoe; Seiichiro Aoe, 8-9-406 Shinsayama 2-chome, Satana, all of Japan

[21] Appl. No.: 08/532,399

[22] Filed: Sep. 22, 1995

[30] Foreign Application Priority Data

Sep. 30, 1994 [JP] Japan .................................. 6-261609
Jul. 21, 1995 [JP] Japan .................................. 7-207509

[51] Int. Cl.⁶ .................................................. A23C 9/12
[52] U.S. Cl. ........................... 426/42; 426/41; 426/656; 426/657; 426/800
[58] Field of Search ........................... 426/41, 42, 34, 426/656, 580, 55, 56, 657, 800, 801, 810; 435/192

[56] References Cited

U.S. PATENT DOCUMENTS

| | | | |
|---|---|---|---|
| 3,970,520 | 7/1976 | Feldman et al. | 426/34 |
| 4,107,334 | 8/1978 | Jolly | 426/7 |
| 5,149,647 | 9/1992 | Burling | 435/192 |
| 5,516,675 | 5/1996 | Uchida et al. | 426/580 |

FOREIGN PATENT DOCUMENTS

| | | | |
|---|---|---|---|
| 0573668 A1 | 12/1993 | European Pat. Off. | |
| WO 93/13676 | 7/1993 | WIPO | |

OTHER PUBLICATIONS

K. Kussendrager, "Lactoferrin and Lactoperoxydase, Bio-Active Milk Proteins" IFI NR.6, pp. 17–21 (1993).

S. Rudloff et al., "Calcium Retention from Milk–Based Infant Formulas, Whey–Hydrolysate Formula, and Human Milk in Weanling Rhesus Monkeys" *AJDC* 144:360–363 (1990).

*Primary Examiner*—Leslie Wong
*Attorney, Agent, or Firm*—Testa, Hurwitz & Thibeault, LLP

[57] ABSTRACT

A bone reinforcing agent comprising a basic protein fraction or a basic peptide fraction derived from milk as an effective component is described. The basic protein fraction is obtained by passing milk or a raw material derived from milk over a cation exchange resin and eluting the adhered fraction. The basic peptide fraction is obtained by hydrolyzing the basic protein fraction with a protease. The basic protein fraction and basic peptide fraction of the present invention promote the growth of osteoclasts and suppress the resorption of osteoclasts, and thereby strengthening bone when administered orally. The invention is useful for treating or preventing bone diseases such as osteoporosis.

7 Claims, 5 Drawing Sheets

PATTERN OF SDS-PAGE

A; MARKER
B; BASIC PROTEIN FRACTION
C; HYDROLYSATE OF B WITH PEPSIN
D; HYDROLYSATE OF B WITH PEPSIN-PANCREATIN
E; MARKER

BONE REINFORCING AGENT AND FOODS AND DRINKS PRODUCT CONTAINING THE SAME

BACKGROUND OF THE INVENTION

1. Field of the Invention

The present invention relates to a bone reinforcing agent and food and drink products containing the same, exhibiting a bone reinforcing activity. Because the bone reinforcing agent and the food and drink products containing the same of the present invention exhibit the effects of promoting the growth of osteoblasts and suppressing bone resorption by osteoblasts, they are useful in treating or preventing various bone diseases such as osteoporosis, bone fractures, rheumatism, and arthritis.

2. Description of the Background Art

In recent years, the incidence of bone diseases such as osteoporosis, bone fractures, lumbago, and the like, have increased along with the progressive increase in the elderly population. These diseases are caused by insufficient calcium intake, decreased calcium absorption hormonal imbalance postmenopause, and the like. Increasing the peak bone mass, or the total amount of bone in the body, is considered to be effective in preventing bone diseases such as osteoporosis, bone fractures, lumbago, and the like in aged people. Increasing the peak bone mass is equivalent to strengthening the bone. Controlling bone resorption is also considered to be effective in preventing osteoporosis. Bone synthesis is characterized by a repeated balanced formation-resorption cycle which is called remodeling. Hormonal imbalance postmenopause causes bone resorption to predominate over bone formation, resulting in osteoporosis. Accordingly, bones are reinforced by controlling bone resorption and maintaining bone mass at a certain level.

Various calcium agents, such as calcium salts (e.g. calcium carbonate, calcium lactate or calcium phosphate), milk or whey calcium, and natural calcium agents (e.g. cattle bone meal or egg shell), and the like, are used to strengthen the bones. These agents are individually administered or added to foods or drinks together with other additives, such as casein phosphopeptide which have the effect of increasing calcium absorption. However, more than half of the calcium salts and natural calcium administered are said to be excreted without being absorbed by the body. Even if absorbed, calcium may not necessarily be utilized for the improvement of bone metabolism or for the reinforcement of bones because the affinity of calcium for bone differs according to the form of the calcium and types of other nutrients which are taken together with calcium. Vitamin $D_3$, calcitonin preparations, estrogen preparations, and the like are known as treatments for osteoporosis or reinforcing bones. In addition, new drugs such as bisphosphonate preparations are under development. Administration of these drugs, however, may be accompanied by side effects such as ear noises, headache, and anorexia. Furthermore, the addition of these drugs to food or drink is currently infeasible due to safety, and cost considerations. Therefore, the development of a bone reinforcing agent, or a food or drink product containing a bone reinforcing agent, which can be orally administered over an extended period of time and which directly exhibits the bone growth promoting effect or the bone resorption suppressing effect, and is effective in the treatment or prevention of the osteoporosis, is desirable.

In view of the above-mentioned problems, the present inventors have undertaken extensive research into the substances contained in various raw food materials which exhibit a bone reinforcing effect. This research has resulted in the finding that a basic protein fraction derived from milk or basic peptide fractions obtained by hydrolyzing the basic protein fraction with a protease, such as pepsin or pancreatin, exhibit the effects of promoting growth of osteoblasts and suppressing resorption of osteoclasts, and can strengthen bone when administered orally. The inventors of the present invention have found that the basic protein fractions and the basic peptide fraction can be used as a bone reinforcing agent or as an effective component for bone reinforcing food and drinks. These findings have led to the present invention.

SUMMARY OF THE INVENTION

Accordingly, an object of the present invention is to provide a bone reinforcing agent and a food or drink product containing the same, exhibiting the effects of promoting growth of osteoblasts and suppressing resorption of osteoclasts, thereby strengthening bone without causing side effects.

The object of the present invention is to obtain a bone reinforcing agent or a food or drink product containing the same which contains a basic protein fraction derived from milk or a basic peptide fraction obtained by hydrolyzing the basic protein fraction with a protease.

Specifically, the present invention relates to a bone reinforcing agent which contains a basic protein fraction derived from milk or a basic peptide fraction obtained by hydrolyzing this basic protein fraction with a protease as an effective component.

The present invention further relates to a bone reinforcing food or drink product which contains the basic protein fraction or the basic peptide fraction, as an effective component.

Other objects, features and advantages of the invention will hereinafter become more readily apparent from the following description.

DETAILED DESCRIPTION OF THE INVENTION AND PREFERRED EMBODIMENTS

Figure 1:
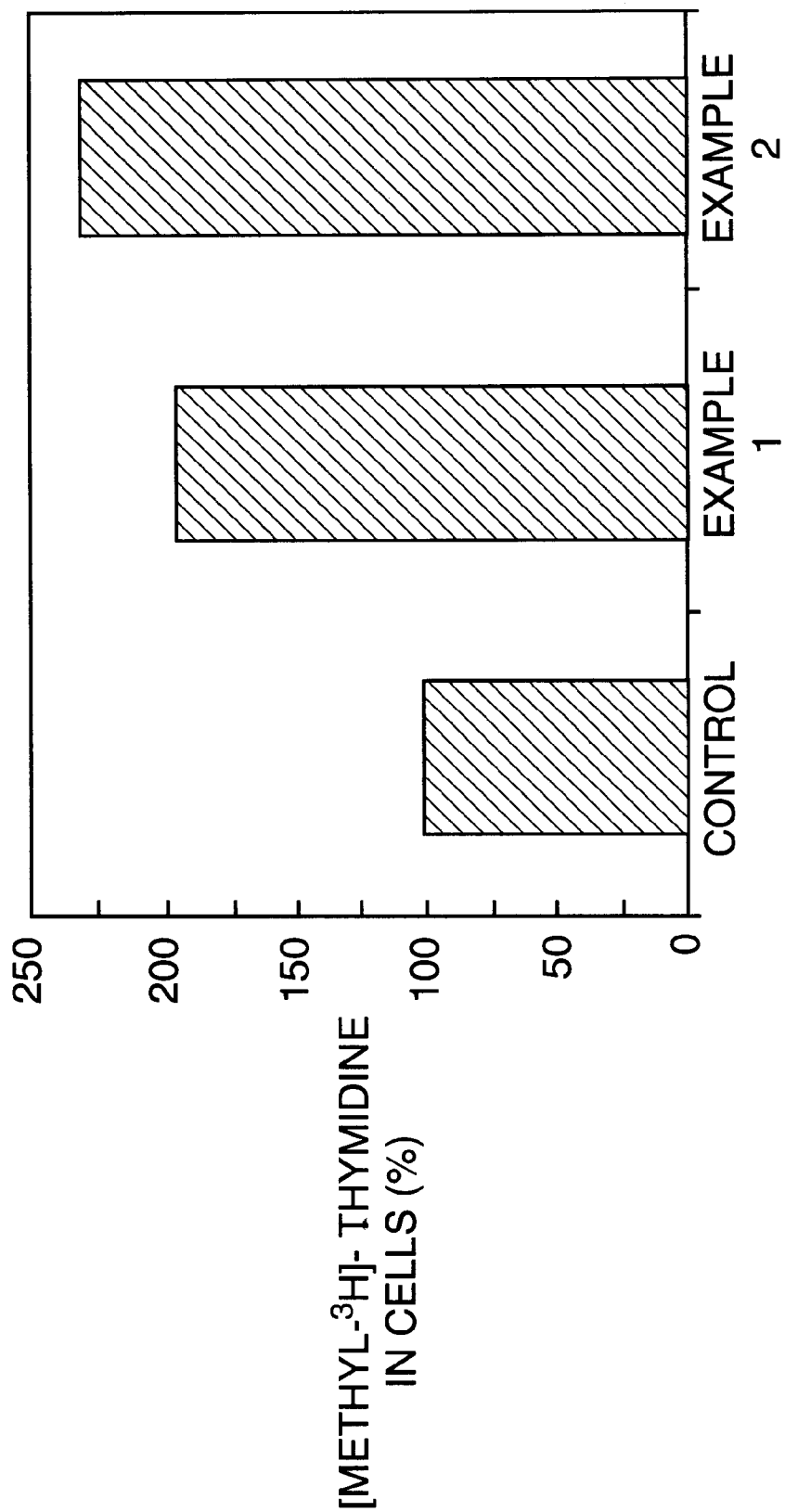
FIG. 1 shows the osteoblast growth promoting activity of the basic protein fraction of the present invention in Test Example 5.

A feature of the present invention is to provide a basic protein fraction derived from milk or a basic peptide fraction obtained by hydrolyzing the basic protein fraction with a protease, as an effective component of a bone reinforcing agent or a food or drink containing the same. The basic protein fraction can be obtained from the milk of a mammal such as a cow, human, goat, sheep, and the like. The basic peptide fraction can be obtained by hydrolyzing the basic protein fraction with a protease. These fractions act directly on the bone to exhibit a bone reinforcing effect and a bone resorption suppressing effect, and thereby strengthen the bone. As later described in detail in the Test Examples 1–4, the basic protein fraction derived from milk has the following characteristics:

1) It comprises several proteins having molecular weights in the range of 3,000–80,000 by SDS-PAGE.

2) It consists of 95% or more protein, with small amounts of fatty acids and ash components.

3) The major proteins are lactoferrin and lactoperoxidase.

4) 15% or more of the amino acids for the proteins are basic amino acids such as lysine, histidine, arginine, and the like.

The basic protein fraction can be obtained, for example, by contacting a raw material derived from milk, such as skim milk or whey, with a cation exchange resin in order to adhere basic proteins, eluting the adhered basic protein fractions with an eluent having a salt content of 0.1–1.0 M, desalting and concentrating the collected fractions using a reverse osmosis (RO) membrane or by electrodialysis (ED) and, optionally, drying the desalted and concentrated product. Other methods known in the art for obtaining the basic protein fraction include a method whereby milk or the raw material derived from milk is adhered to the cation exchange resin by contacting the former to the cation exchange resin and eluting the adhered basic protein fraction with an eluent with a pH of 5 or greater and an ion strength of 0.5 or greater (Japanese Patent Application Laid-open (kokai) No. 202098/1993); a method using arginic acid gel (Japanese Patent Application Laid-open (kokai) No. 246198/1986); a method of obtaining the basic protein fraction from whey using inorganic porous particles (Japanese Patent Application Laid-open (kokai) No. 86839/1989); a method of obtaining the basic protein fraction from milk using a sulfated ester (Japanese Patent Application Laid-open (kokai) No. 255300/1988); and the like. Any basic protein fraction obtained by any one of these methods can be used in the present invention.

The basic peptide fraction derived from milk has the same amino acid composition as the basic protein fraction, and can be obtained as a peptide composition with an average molecular weight of 4,000 Da or less by hydrolysis of the basic protein fraction with a protease such as pepsin, trypsin, chymotrypsin, or the like, and further, optionally, with other proteases such as pancreatin or the like.

The basic protein fraction or the basic peptide fraction, which is the effective component of the bone reinforcing agent of the present invention, may be administered as is or in suitable forms such as powder, granules, tablets, capsules, drinks, and the like, by conventional methods. Furthermore, it is possible to administer the basic protein fraction or the basic peptide fraction, as it is or after it has been processed into suitable forms, into nutrients, drinks, or foods, to strengthen the bones by promoting bone formation or suppressing bone resorption. Because the milk-derived basic protein fraction and the basic peptide fraction of the present invention are comparatively stable with respect to heat, it is possible to sterilize the raw materials containing these fractions with heat by a conventional method.

The dose of the basic protein fraction or the basic peptide fraction of the present invention depends on the age of the patient, the effects desired from the treatment, and the disease conditions. Tests using rats confirmed that the amount of the basic protein fraction or the basic peptide fraction for exhibiting the bone reinforcing effect is 0.1% by weight or more in feed. Accordingly, the bone reinforcing effect can be illicited by administering the basic protein fraction or the basic peptide fraction at a dose of 0.5 g/day or more to an adult, who generally takes 500 g/day on a dry basis of food and drink.

Because the bone reinforcing agent and the food or drink containing the same of the present invention promote bone formation and suppress bone resorption, the bones are reinforced if they are administered. Accordingly, the bone reinforcing agent and the food or drink containing the same are useful for treating or preventing various bone diseases, such as osteoporosis, bone fractures, rheumatism, and arthritis and are particularly effective in treating or preventing osteoporosis. Further, it is possible to increase the peak bone mass in the growth period by administering the bone reinforcing agent or a food or drink containing the same of the present invention to infants and children.

EXAMPLE 1

A column (diameter: 5 cm, height: 30 cm), packed with 400 g of a cation exchange resin, sulfonated chytopal (trademark, manufactured by Fuji Spinning Co., Ltd.), was thoroughly washed with deionized water. 40 of unsterilized skim milk (pH 6.7) was passed through this column at a flow rate of 25 ml/min, after which the column was thoroughly washed with deionized water. The basic protein fraction adhered to the resin was eluted with a 0.02 M carbonate buffer (pH 7.0) containing 0.98 M sodium chloride. The eluate was desalted and concentrated with an RO membrane and freeze-dried to obtain 21 g of powdered basic protein fraction.

TEST EXAMPLE 1

Figure 6:
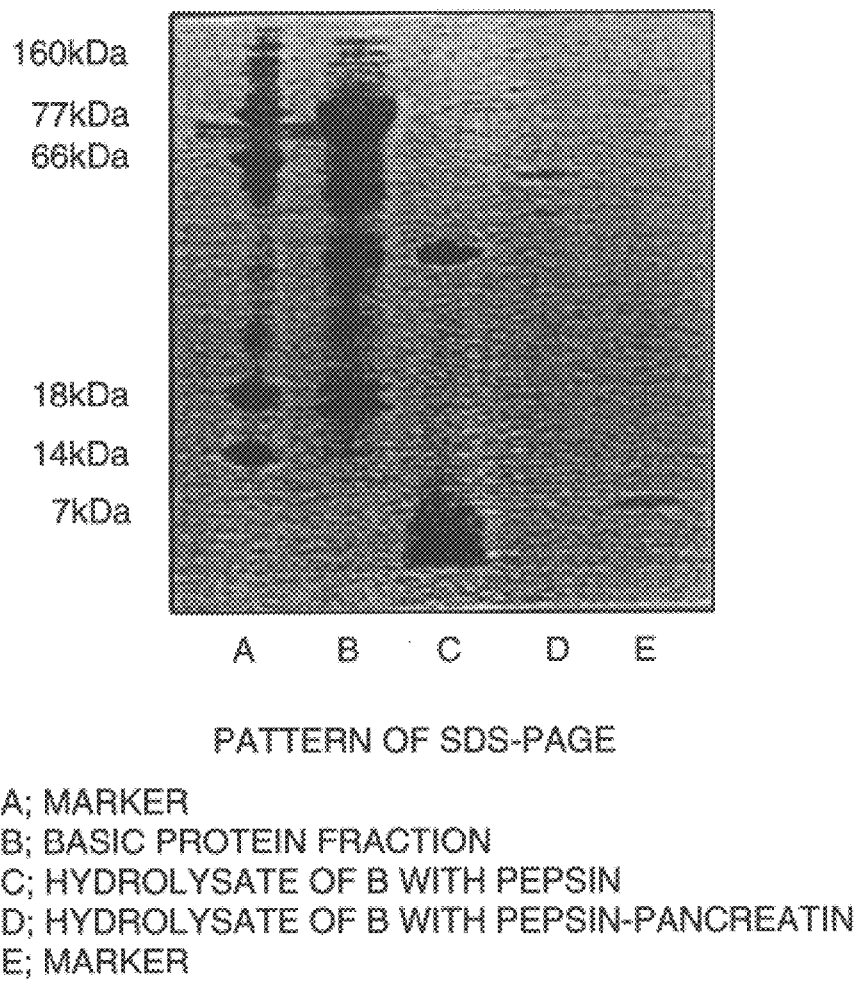
FIG. 6 is an sodium dodecyl sulfate-polyacrylamide gel electrophoresis (SDS-PAGE) pattern of the basic protein fraction of the present invention in Test Example 1.

The molecular weight of the basic protein fraction obtained in Example 1 was measured by SDS-PAGE and was found to be in the range of 3,000–80,000. The results are shown in FIG. 6.

TEST EXAMPLE 2

The composition of the basic protein fraction prepared in Example 1 was analyzed. The results are shown in Table 1. These results indicate that almost all components in the fraction were proteins.

TABLE 1

|  | (wt. %) |
|---|---|
| Water | 1.06 |
| Proteins | 96.50 |
| Fats | 0.56 |
| Ash | 0.27 |
| Others | 1.61 |

TEST EXAMPLE 3

The composition of the proteins in the basic protein fraction prepared in Example 1 was analyzed. The results are shown in Table 2. These results indicate that the basic protein fraction contains 40 wt. % or more of lactoferrin and 40 wt. % or more of lactoperoxidase.

TABLE 2

|  | (wt. %) |
| --- | --- |
| Lactoferrin | 42.5 |
| Lactoperoxidase | 45.6 |
| Insulin-like growth factor-I factor-I | 0.005 |
| Others | 11.895 |

TEST EXAMPLE 4

The basic protein fraction obtained in Example 1 was hydrolyzed with 6N hydrochloric acid at 110° C. for 24 hours and analyzed with an amino acid analyzer (L-8500, trademark, manufactured by Hitachi, Co. Ltd.). The results are shown in Table 3. These results indicate that the basic protein fraction contains about 15 wt. % or more of basic amino acids out of the total amino acids.

TABLE 3

|  | (wt. %) |
| --- | --- |
| Aspartic acid | 10.1 |
| Serine | 5.3 |
| Glutamic acid | 12.3 |
| Proline | 4.7 |
| Alanine | 5.7 |
| Leucine | 10.2 |
| Lysine | 8.4 |
| Histidine | 2.5 |
| Arginine | 7.2 |
| Others | 33.6 |

EXAMPLE 2

A column (diameter: 100 cm, height: 10 cm), packed with 30 kg of a cation exchange resin, SP-Toyopal (trademark, manufactured by Toso Co. Ltd.), was thoroughly washed with deionized water. A cheese whey, sterilized by heating at 121° C. for 30 seconds, was passed through the column at a flow rate of 10 l/min, after which the column was thoroughly washed with deionized water. The basic protein fraction adhered to the resin was eluted with a 0.1 M citrate buffer (pH 5.7) containing 0.9 M sodium chloride. The eluate was desalted and concentrated using the ED method and freeze-dried to obtain 183 g of powdered basic protein fraction.

TEST EXAMPLE 5

The osteoblast growth promoting activity of the basic protein fraction obtained in Example 2 was measured.

Osteoblasts (MC3T3-E1) were cultured in a 96-well flat bottom petri dish for 18 hours in α-MEM culture medium (Flow Laboratories Inc.) containing 0.2% calf serum. For the culture, 2 μl of a solution prepared by dissolving the basic protein fraction obtained in Example 1 or 2 to a concentration of 0.5% was added to 100 μl of the medium. After culturing, [methyl-$^3$H]-thymidine was added to measure the osteoblast growth promoting. The [methyl-$^3$H]-thymidine in the cells was measured after two hours (Protocol for New Experiments of Cell Technology, pp 319–320 (1993), The University of Tokyo, Medical Scientific Research Center, Cancer Research Institute). The results of the experiment are shown in FIG. 1, in which the cell growth promoting activity is indicated by the radioactivity (in percent) of the medium to which the basic protein fraction was added, taking the radioactivity of the medium to which no basic protein fraction had been added as 100%. The FIG. 1 shows that the osteoblast growth promoting activity in samples to which the basic protein fraction obtained in Example 1 or 2 was added was almost twice that of the sample to which no basic protein fraction had been added.

TEST EXAMPLE 6

The osteoblast growth promoting activity and the effect of suppressing osteoclast resorption were investigated for (i) the basic protein fraction prepared in Example 1, (ii) the basic peptide fraction obtained by the hydrolysis of the basic protein fraction prepared in Example 1 with pepsin, and (iii) the basic peptide fraction obtained by the hydrolysis of the basic protein fraction prepared in Example 1 with pepsin and pancreatin, according to the inverted gut sac method (Shiroh Gotoh et al. Nutrition Experiments with Small Animals, pp 83–85 (1980).

The small intestine from a mature rat was extirpated after overnight fasting and 7 cm of the duodenum from the pyloric region of the stomach was turned inside out. A Ringer's solution was injected into this inverted gut sac and then ligated. The inverted gut sac was then incubated in an external solution made up of the Ringer's solution (control), or (a) the Ringer's solution and 1% of the basic protein fraction prepared in Example 1, (b) the Ringer's solution and 1% of the basic peptide fraction obtained by hydrolysis of the basic protein fraction prepared in Example 1 with pepsin, or (c) the Ringer's solution and 1% of the basic peptide fraction obtained by hydrolysis of the basic protein fraction prepared in Example 1 with pepsin and pancreatin, and incubated at 37° C. while oxygen gas was bubbled through the solution. After one hour, liquid was collected from the inside of each inverted gut sac to determine the osteoblast growth promoting activity in the same manner as in Test Example 5.

Femora were extirpated from rabbits (age: 10 days) and the soft tissues were removed. All the bone marrow cells containing osteoclasts, prepared by mechanically pulverizing the femora in a medium containing 5% FBS, were plated over a piece of ivory at 200,000 cells/ml. The cells were cultured for two days with 10% of a solution prepared by diluting the liquid collected from the insides of each inverted gut sac threefold. Bone resorption pits created on the ivory were stained with hematoxylin and counted to determine the effect of suppressing osteoclast resorption (Kanji Seno, et al. The Manual for Animal Culture Cells for Different Research Themes, pp 199–200 (1993)).

Figure 2:
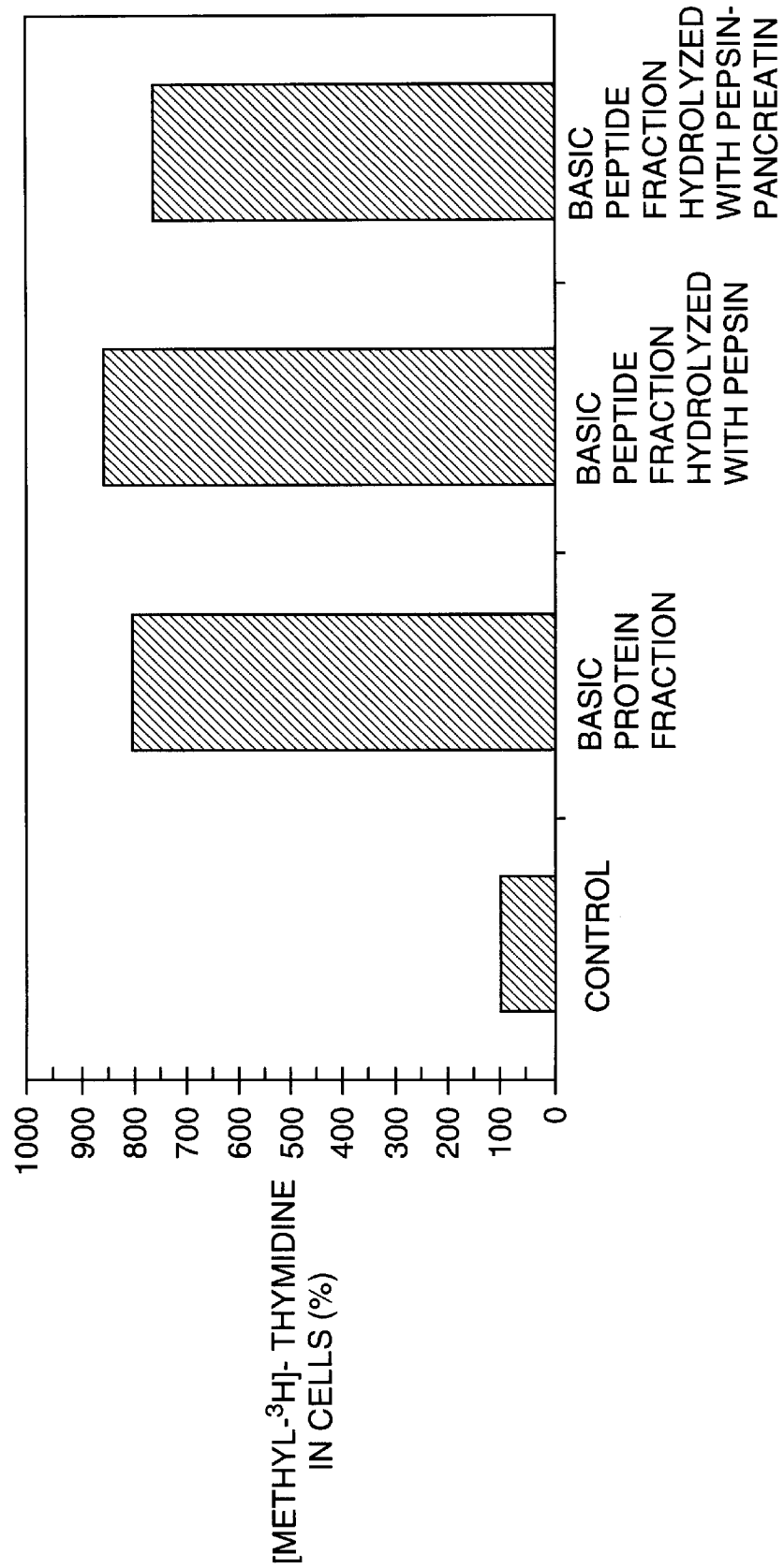
FIG. 2 shows the osteoblast growth promoting activity of the basic protein fraction and the basic peptide fraction of the present invention in Test Example 6.
Figure 3:
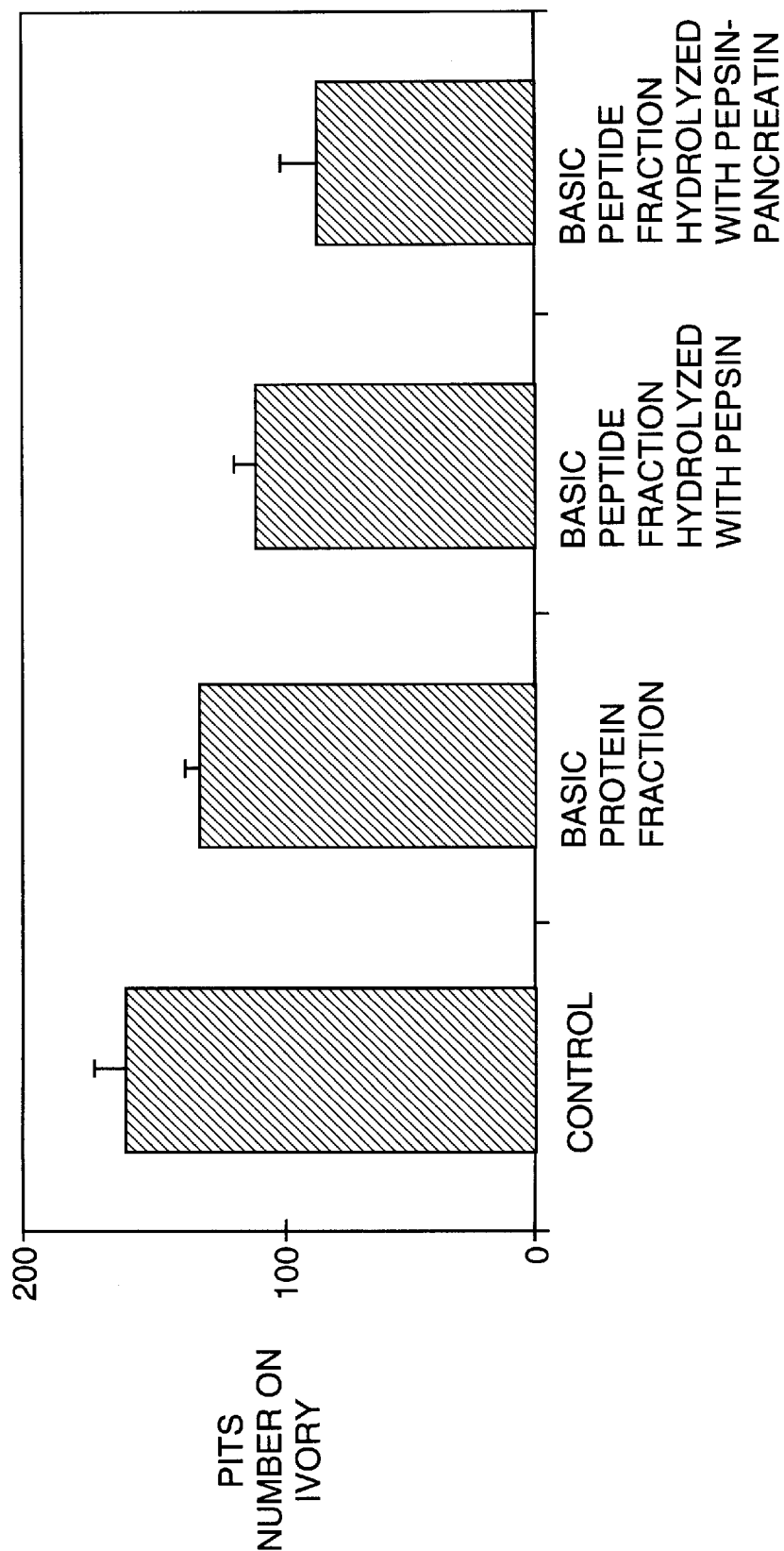
FIG. 3 shows the osteoclast bone resorption suppressing activity of the basic protein fraction and the basic peptide fraction of the present invention in Test Example 6.

The results are shown in FIGS. 2 and 3. In FIG. 2, osteoblast cell growth activity is indicated in terms of the increased radioactivity (in percent) relative to the radioactivity (100%) of the group for which the liquid was collected from the insides of each inverted gut sac incubated in Ringer's solution and held for one hour (control). In the same manner, in FIG. 3, suppressed osteoclast resorption is represented by the increased number of pits relative to the number of pits of the group for which the liquid was collected from the insides of each inverted gut sac incubated in Ringer's solution and held for one hour (control).

Greater osteoblast growth promoting activity and greater suppression of the osteoclast resorption were confirmed in all groups using (a) Ringer's solution and 1% basic protein fraction prepared in Example 1, (b) Ringer's solution and 1% basic peptide fraction obtained by the hydrolysis of the basic protein fraction prepared in Example 1 with pepsin, or (c) Ringer's solution and 1% basic peptide fraction obtained by the hydrolysis of the basic protein fraction prepared in Example 1 with pepsin and pancreatin, as the external solutions for the inverted gut sac, as compared with those of the group in which only the Ringer's solution was used as the external solution. These results confirmed that the effective component of the bone reinforcing agent of the present invention can pass through the gastrointestinal tract.

TEST EXAMPLE 7

The bone reinforcing effect of the basic protein fraction obtained in Example 2 was measured in experiments using animals.

SD strain female rats (age: 6 weeks) were used for the experiment. The rats were fed normally for 1 week prior to the ovarneoctomized operation. Then, the animals were fed with a calcium deficient diet for 5 weeks. Osteoporosis was apparently induced in the rats fed with a calcium deficient diet after ovariectomy. The osteoporosis-induced rats were grouped into (A) a control group, (B) 0.1 wt. % basic protein fraction dosing group, (C) 0.5 wt. % basic protein fraction dosing group, (D) 1.0 wt. % basic protein fraction dosing group, each group consisting of 6 rats. Animals of each group were fed for 4 weeks with the test diets shown in Table 4. All diets were adjusted with casein so that they contained an equivalent amount (17.06%) of nitrogen. In addition, 300 mg of calcium, 230 mg of phosphorous, and 50 mg of magnesium were added to each 100 g of food.

TABLE 4

| | (wt. %) | | | |
|---|---|---|---|---|
| | A | B | C | D |
| Casein | 20.0 | 19.9 | 19.4 | 18.9 |
| Corn starch | 15.0 | 15.0 | 15.0 | 15.0 |
| Cellulose | 5.0 | 5.0 | 5.0 | 5.0 |
| Corn oil | 5.0 | 5.0 | 5.0 | 5.0 |
| Vitamins | 1.0 | 1.0 | 1.0 | 1.0 |
| Minerals | 2.65 | 2.65 | 2.65 | 2.65 |
| Sucrose | 51.05 | 51.05 | 51.15 | 51.15 |
| DL-Methionine | 0.3 | 0.3 | 0.3 | 0.3 |
| Basic protein fraction | — | 0.1 | 0.5 | 1.0 |

Figure 4:
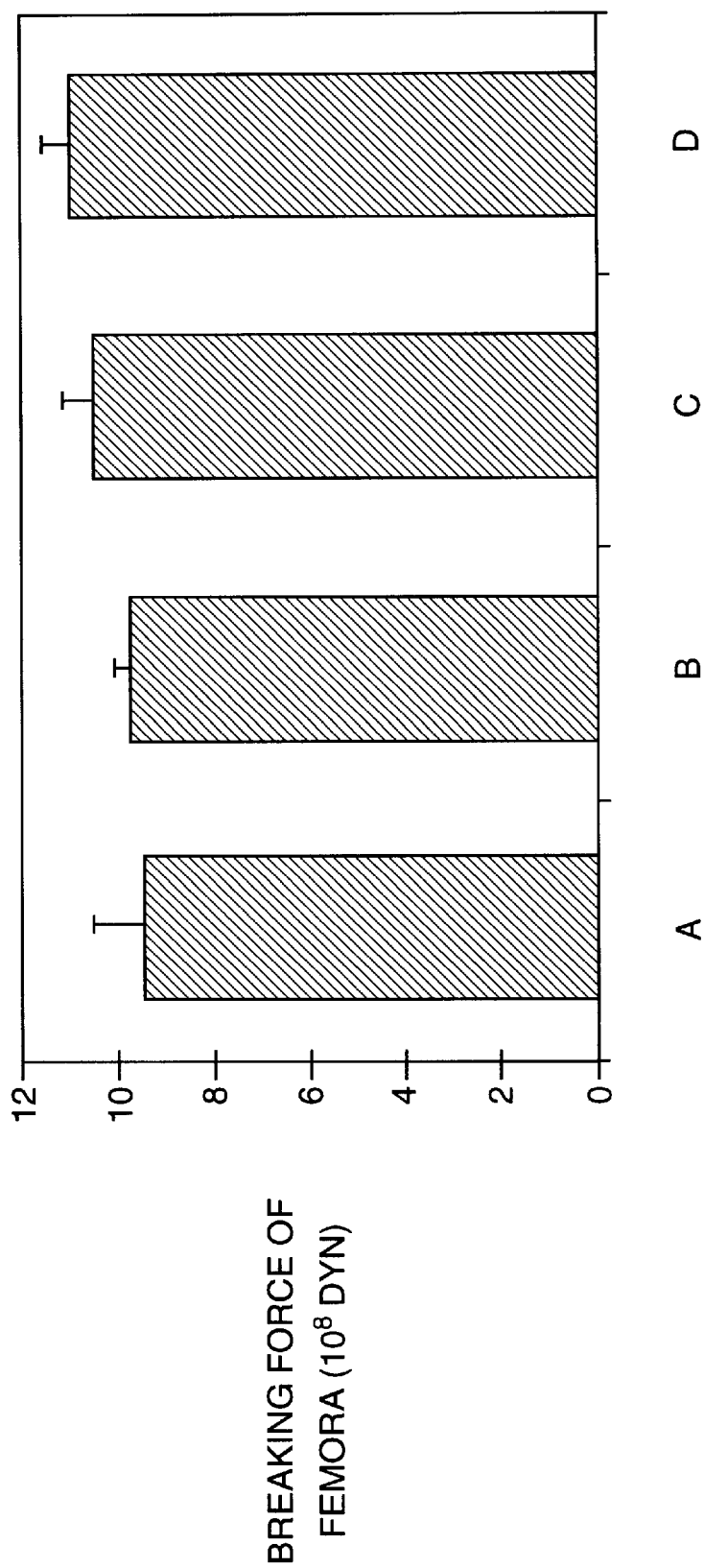
FIG. 4 shows the effect of increasing the breaking force of a femora by the basic protein fraction of the present invention in Test Example 7.
Figure 5:
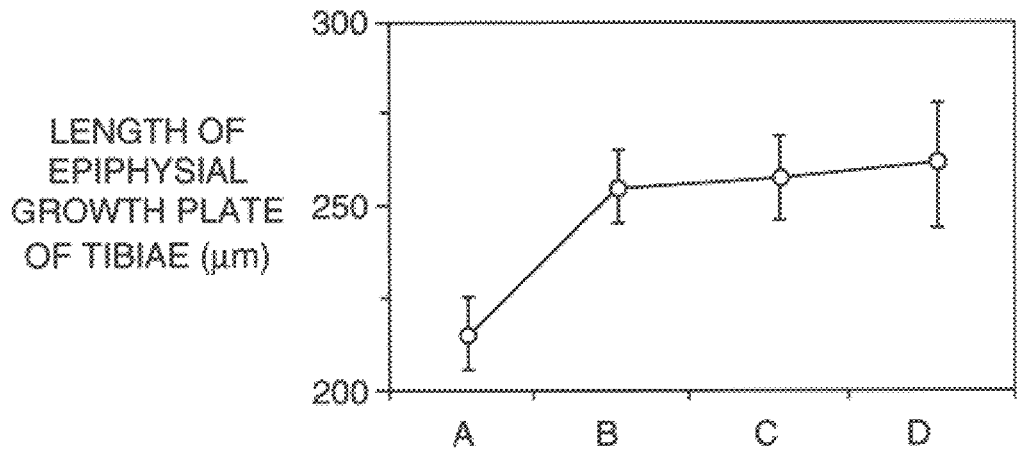
FIG. 5 shows the growth promoting effect on tibia epiphysial growth plates by the basic protein fraction of the present invention in Test Example 7.

After 4 weeks, both the femora and tibiae were extirpated. The breaking force of the femora was measured using a bone fracture properties measuring device (Rheometer Max RX-1600, trademark, manufactured by Aitekno Co. Ltd.). The tibiae were electrically demineralized and stained with Hematoxylin-Eosin in order to measure the length of the epiphysial growth plates. The results are shown in FIGS. 4 and 5. The groups to which the basic protein fraction was administered (groups B to D) exhibited a greater breaking force of femora than the control group (group A). Further, the greater the concentration of basic protein fraction, the greater the values of femora breaking strength. Also, the lengths of the tibia epiphysial growth plates were significantly and dose-dependently longer in the groups to which the basic protein fraction was administered (groups B to D) compared to the control group (group A).

EXAMPLE 3

A bone reinforcing drink of the composition shown in Table 5 was prepared.

TABLE 5

| | (wt. %) |
|---|---|
| Mixed isomerized sugar | 15.0 |
| Fruit juice | 10.0 |
| Citric acid | 0.5 |
| Powder of basic protein fraction (Example 1) | 0.5 |
| Spice | 0.1 |
| Calcium | 0.1 |
| Water | 73.5 |

EXAMPLE 4

A paste with a composition shown in Table 6 was formed and baked to make a bone reinforcing biscuit.

TABLE 6

| | (wt. %) |
|---|---|
| Wheat | 50.0 |
| Sugar | 20.0 |
| Salt | 0.5 |
| Margarine | 12.5 |
| Egg | 12.5 |
| Water | 2.5 |
| Sodium bicarbonate | 0.15 |
| Ammonium bicarbonate | 0.2 |
| Calcium carbonate | 0.45 |
| Powder of basic protein fraction (Example 1) | 1.2 |

EXAMPLE 5

Tablets of bone reinforcing agent with a composition shown in Table 7 were prepared.

TABLE 7

| | (wt. %) |
|---|---|
| Hydrous crystalline glucose | 73.5 |
| Fraction prepared in the Example 2 | 20.0 |
| Calcium | 5.0 |
| Sugar ester | 1.0 |
| Perfume | 0.5 |

Numerous modifications and variations of the present invention are possible in light of the above teachings. It is therefore to be understood that within the scope of the appended claims, the invention may be practiced otherwise than as specifically described herein.

We claim:

1. A bone reinforcing agent comprising, as an effective component, a basic protein fraction derived from milk having an amino acid composition containing at least 15% by weight of basic amino acids, said protein fraction containing at least 95% by weight of at least two different proteins having molecular weights of 3,000–80,000 Da, as measured by SDS-PAGE.

2. The bone reinforcing agent according to claim 1, wherein the basic protein fraction derived from milk is obtained by contacting milk or raw material derived from milk to a cation exchange resin to adhere the basic protein and eluting the adhered fraction with an eluent having a base concentration of 0.1 M to 1.0 M.

3. A bone reinforcing agent comprising, as an effective component, a basic peptide fraction having an average molecular weight of 4,000 Da or less, said peptide fraction obtained by hydrolyzing a basic protein fraction derived from milk with a protease, said basic protein fraction having an amino acid composition containing at least 15% by weight of basic amino acids and containing at least 95% by weight of at least two different proteins having molecular weights of 3,000–80,000 Da, as measured by SDS-PAGE.

4. The bone reinforcing agent according to claim 3, wherein the protease is selected from the group consisting of pepsin, trypsin, and chymotrypsin.

5. The bone reinforcing agent according to claim 3, wherein the protease is pancreatin and at least one protease selected from the group consisting of pepsin, trypsin, and chymotrypsin.

6. The bone reinforcing agent according to claim 1, which exhibits effects of promoting growth of osteoblasts and suppressing resorption of osteoclasts.

7. A food or drink composition comprising the basic protein fraction derived from milk defined in claims 1 or 3.

* * * * *

UNITED STATES PATENT AND TRADEMARK OFFICE
CERTIFICATE OF CORRECTION

PATENT NO. : 5,932,259

DATED : August 3, 1999

INVENTOR(S) : Ken Kato, et al.

It is certified that error appears in the above-identified patent and that said Letters Patent is hereby corrected as shown below:

On the Title page, and in col. 1, line 1;

Item [54] should read --BONE REINFORCING AGENT AND FOOD AND DRINK PRODUCTS CONTAINING THE SAME--.

Signed and Sealed this

Nineteenth Day of September, 2000

Attest:

Q. TODD DICKINSON

*Attesting Officer*     Director of Patents and Trademarks